(12) United States Patent
Garabadian

(10) Patent No.: US 6,983,752 B2
(45) Date of Patent: Jan. 10, 2006

(54) DENTAL APPLIANCE FOR THE TREATMENT OF SLEEP DISORDERS

(75) Inventor: Charles Garabadian, Cumming, GA (US)

(73) Assignee: Sleep Sound Services ZZZ, Seneca, SC (US)

(*) Notice: Subject to any disclaimer, the term of this patent is extended or adjusted under 35 U.S.C. 154(b) by 121 days.

(21) Appl. No.: 10/798,167

(22) Filed: Mar. 11, 2004

(65) Prior Publication Data

US 2005/0199247 A1  Sep. 15, 2005

(51) Int. Cl.
A61F 5/56 (2006.01)

(52) U.S. Cl. .................. 128/848; 128/861; 602/902

(58) Field of Classification Search ............... 128/848, 128/859, 861, 862, 846; 602/902; 433/6, 433/37, 41, 42
See application file for complete search history.

(56) References Cited

U.S. PATENT DOCUMENTS

| | | | | |
|---|---|---|---|---|
| 3,107,668 A | * | 10/1963 | Thompson | .................. 128/861 |
| 3,536,069 A | * | 10/1970 | Gores | .......................... 128/861 |
| RE28,667 E | * | 12/1975 | Gores | .......................... 128/861 |
| 4,173,219 A | * | 11/1979 | Lentine | ........................ 128/861 |
| 4,541,800 A | | 9/1985 | Bernstein | |
| 5,499,633 A | | 3/1996 | Fenton | |
| 5,570,704 A | | 11/1996 | Buzzard et al. | |
| 5,823,193 A | | 10/1998 | Singer et al. | |
| 5,868,138 A | | 2/1999 | Halstrom | |
| 5,884,628 A | | 3/1999 | Hilsen | |
| 5,895,218 A | * | 4/1999 | Quinn et al. | .................. 433/42 |
| 5,941,247 A | | 8/1999 | Keane | |
| 5,970,981 A | * | 10/1999 | Ochel | ......................... 128/859 |
| 6,041,784 A | | 3/2000 | Halstrom | |
| 6,055,986 A | | 5/2000 | Meade | |
| 6,109,265 A | | 8/2000 | Frantz et al. | |
| 6,412,489 B1 | * | 7/2002 | Sue | ............................ 128/848 |
| 6,820,623 B2 | * | 11/2004 | Cook | ......................... 128/859 |
| 2003/0056797 A1 | | 3/2003 | Strong | |

* cited by examiner

Primary Examiner—Fadi H. Dahbour
(74) Attorney, Agent, or Firm—McNair Law Firm, P.A.

(57) ABSTRACT

An upper tray for receiving the maxillary teeth and a lower tray for receiving the mandibular teeth. Upper bite pads carried by the upper tray and lower bite pads carried by the lower tray. The lower bite pads located anterior to the upper bite pads so that the lower bite pads are free to engage the maxillary occlusal surface of the upper tray, and the upper bite pads are free to engage the mandibular occlusal surface of the lower tray to maintain the occlusal surfaces of the trays in a predetermined spaced relationship. The upper and lower bite pads are arranged to abut each other for advancing the mandible and preventing posterior movement of the mandible while allowing limited vertical and lateral movement. The bite pads are releasably carried by the trays for interchanging different sizes of pads to customize the appliance to the needs of the user's mouth.

19 Claims, 6 Drawing Sheets

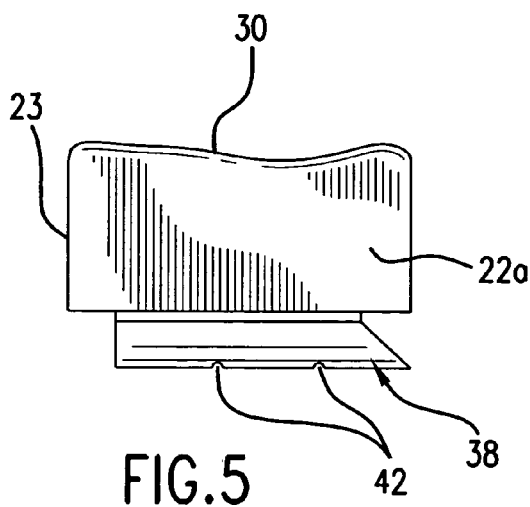
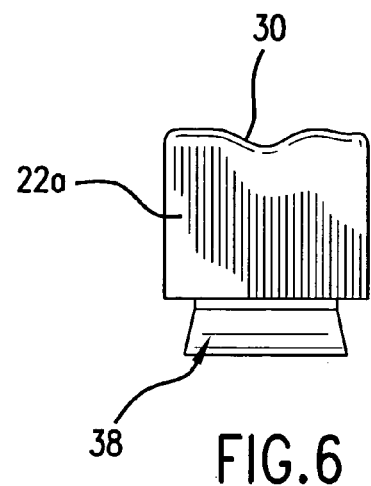
FIG.5　　FIG.6
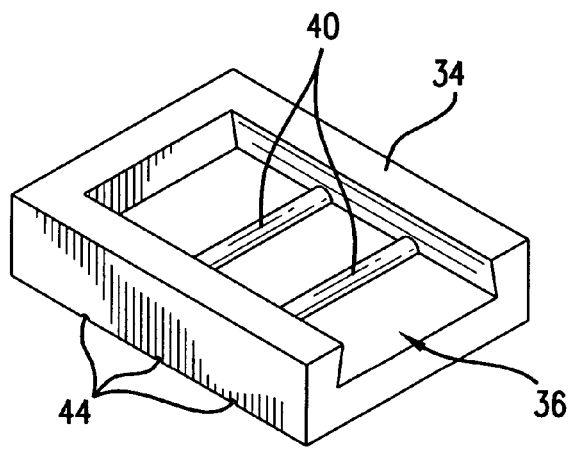
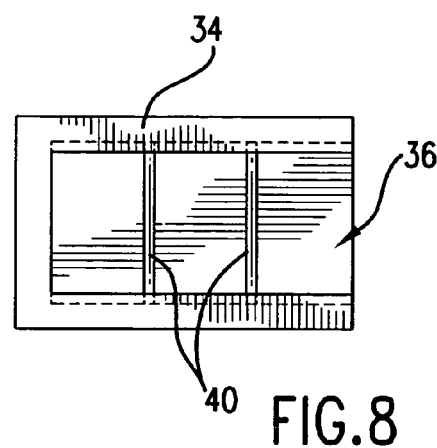
FIG.7　　FIG.8
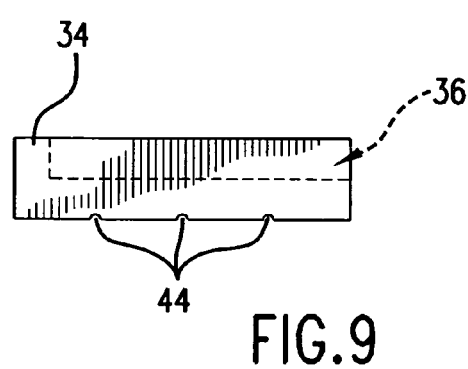
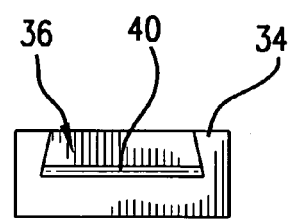
FIG.9　　FIG.10

DENTAL APPLIANCE FOR THE TREATMENT OF SLEEP DISORDERS

FIELD OF THE INVENTION

The present invention relates generally to oral dental appliances, and more particularly, to a dental appliance worn while sleeping for the prevention and alleviation of sleep disorders. The appliance spaces the occlusal surfaces of a user's maxillary and mandibular teeth, and advances the mandible to prevent posterior movement of the lower jaw while allowing for limited vertical and lateral movement.

BACKGROUND OF THE INVENTION

It is known in the prior art that an oral appliance which opens the jaws and advances the mandible can help reduce incidences of snoring, sleep apnea, and other breathing problems associated with sleep. While the prior art is replete with such devices, many are uncomfortable due to their rigid construction, which often leads to joint pain in the jaws. Some of the devices represented in the prior art are adjustable to move the jaw forward or back, or adjust the spacing between the jaws, but are still generally rigid devices. Further, these devices are not fully customizable by the user and require professional adjustment to fit the appliance to the user's needs. Additionally, such adjustments typically only modify the appliance to a new fixed position and do not allow for necessary lateral and vertical movement of the jaws to prevent joint pain.

As is acknowledged by the prior art, there is no existing appliance that is totally adjustable, both in the amount of forward movement and vertical opening. For most appliances, adjustments are made by either soldering on spacers or grinding away plastic from the appliance. Once such modifications are made, they are often permanent until further modifications are performed by a dentist or other health care professional. Fitting such an appliance typically requires numerous trips to the dentist at ever increasing costs. Other more adjustable appliance simply advance and space the lower jaw through set incremental steps. Such devices rigidly interlock the maxillary and mandibular portions of the appliance together, preventing any vertical or lateral movement of the jaw, which can be unnecessarily painful to most users. Additionally, many of these devices do not provide an opening at the front of the mouth through which the tongue may extend to prevent airway constriction that causes many of the sleep breathing disorders.

Accordingly, it is an object of the present invention to provide a dental appliance which opens the jaws and advances the mandible to prevent and alleviate sleep disorders.

It is an object of the present invention to provide a dental appliance in which the vertical spacing of the jaws and advancement of the mandible is fully customizable by the user.

It is an object of the present invention to provide a dental appliance in which the maxillary and mandibular portions are not rigidly connected and allows for limited vertical and lateral movement.

It is an object of the present invention to provide a dental appliance that produces an unobstructed opening at the front of the mouth through which the tongue is free to extend to prevent the tongue from moving posteriorly.

SUMMARY OF THE INVENTION

The above objectives are accomplished according to the present invention by providing a dental appliance for spacing the occlusal surfaces of a user's maxillary and mandibular teeth and advancing the mandible that includes an upper tray for receiving the maxillary teeth and a lower tray for receiving the mandibular teeth. At least one upper bite pad is carried by the upper tray having a downward projecting bite surface extended from a maxillary occlusal surface of the upper tray. At least one lower bite pad is carried by the lower tray having an upward projecting bite surface extended from a mandibular occlusal surface of the lower tray. The lower bite pad is located anterior to the upper bite pad within the user's mouth so that the upward projecting bite surface of the lower bite pad is free to engage the maxillary occlusal surface of the upper tray, and the downward projecting bite surface of the upper bite pad is free to engage the mandibular occlusal surface of the lower tray to maintain the occlusal surfaces of the trays in a predetermined spaced relationship. Advantageously, the upper and lower bite pads are arranged to abut each other for advancing the mandible and preventing posterior movement of the mandible while allowing the mandible lateral and vertical flexibility.

In a further advantageous embodiment, the upper and lower bite pads are releasably carried by the trays for interchanging different sizes and shapes of bite pads to customize corrective adjustments resulting from the appliance to the specific needs of the user's mouth.

Preferably, the dental appliance includes an upper base member carried on the maxillary occlusal surface of the upper tray, and a lower base member carried on the mandibular occlusal surface of the lower tray. The upper base member and the lower base member are adapted for releasably interconnecting with the upper and lower bite pads, respectively. The upper and lower base members include a first locking part, and the bite pads include a second locking part adapted for cooperating with the first locking part of the base members to releasably interconnect the pads to the base members. In a preferred embodiment, the first locking part of the base members comprises a dovetailed keyway, and the second locking part of the pads comprises a dovetailed key for engaging the dovetailed keyway.

Advantageously, at least one elastic band interconnects the upper tray with the lower tray to limit separation of the trays and prevent the lower bite pad from avoiding the upper bite pad and moving posteriorly. Also, at least one upper button is carried by the upper tray and at least one lower button is carried by the lower tray. The elastic band engages and extends between the upper and lower buttons to interconnect the trays while allowing for limited vertical movement. Preferably, the elastic band is x-shaped for interconnecting with a plurality of upper and lower buttons carried by the trays.

In a preferred embodiment, the upper and lower trays are adapted to conform to the user's maxillary and mandibular dentitions, respectively, for holding the trays in place against the user's teeth. Additionally, the downward projecting bite surface of the upper bite pad is adapted to conform to the mandibular dentitions in the opposing mandibular occlusal surface of the lower tray for cooperative engagement. Further, the upward projecting bite surface of the lower bite pad is adapted to conform to the maxillary dentitions in the maxillary occlusal surface of the upper tray for cooperative engagement.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 5 shows a side elevation view of a bite pad according to the present invention;

FIG. 6 shows an end view of a bite pad according to the present invention;

FIG. 7 shows a perspective view of a base member according to the present invention;

FIG. 8 shows a top view of a base member according to the present invention;

FIG. 9 shows a side elevation view of a base member according to the present invention;

FIG. 10 shows an end view of a base member according to the present invention;

DETAILED DESCRIPTION OF A PREFERRED EMBODIMENT

Figure 1:
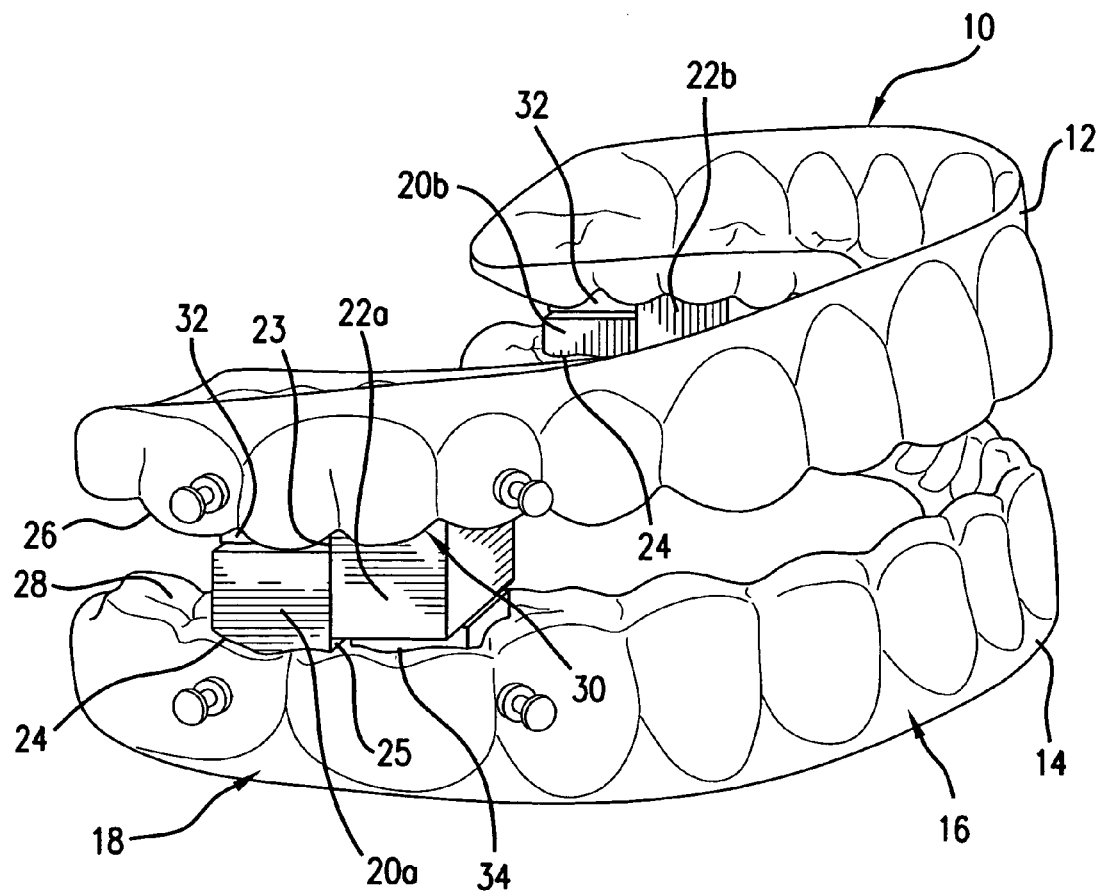
FIG. 1 shows a perspective view of a dental appliance according to the present invention.

With reference to the drawings, the invention will now be described in more detail. Referring to FIG. 1, a dental appliance, designated generally as 10, is shown for spacing the occlusal surfaces of a user's maxillary and mandibular teeth and advancing the mandible.

Appliance 10 includes an upper tray 12 adapted for receiving the maxillary teeth of the upper jaw, and a lower tray 14 adapted for receiving the mandibular teeth of the lower jaw. Both upper tray 12 and lower tray 14 are defined as having an anterior portion, designated generally as 16, which receives the teeth along the front of the jaws, and a posterior portion, designated generally as 18, which receives the teeth along the rear portions of the jaws. Preferably, the trays are made of a co-polyester plastic material or other commonly known plastic used by those skilled in the art. However, the trays are not limited to being made of a specific plastic, but rather may be made of any material suitable to carrying out the present invention. In a preferred embodiment, upper tray 12 and lower tray 14 are molded to conform to the shape of the user's maxillary and mandibular dentitions, respectively. Molding trays 12 and 14 to match the shape of the user's teeth provides a custom fit which is more comfortable for the user to wear and holds the trays in place against the user's teeth in a much more effective manner than if the trays are not molded to the shape of the user's teeth.

Figure 2:
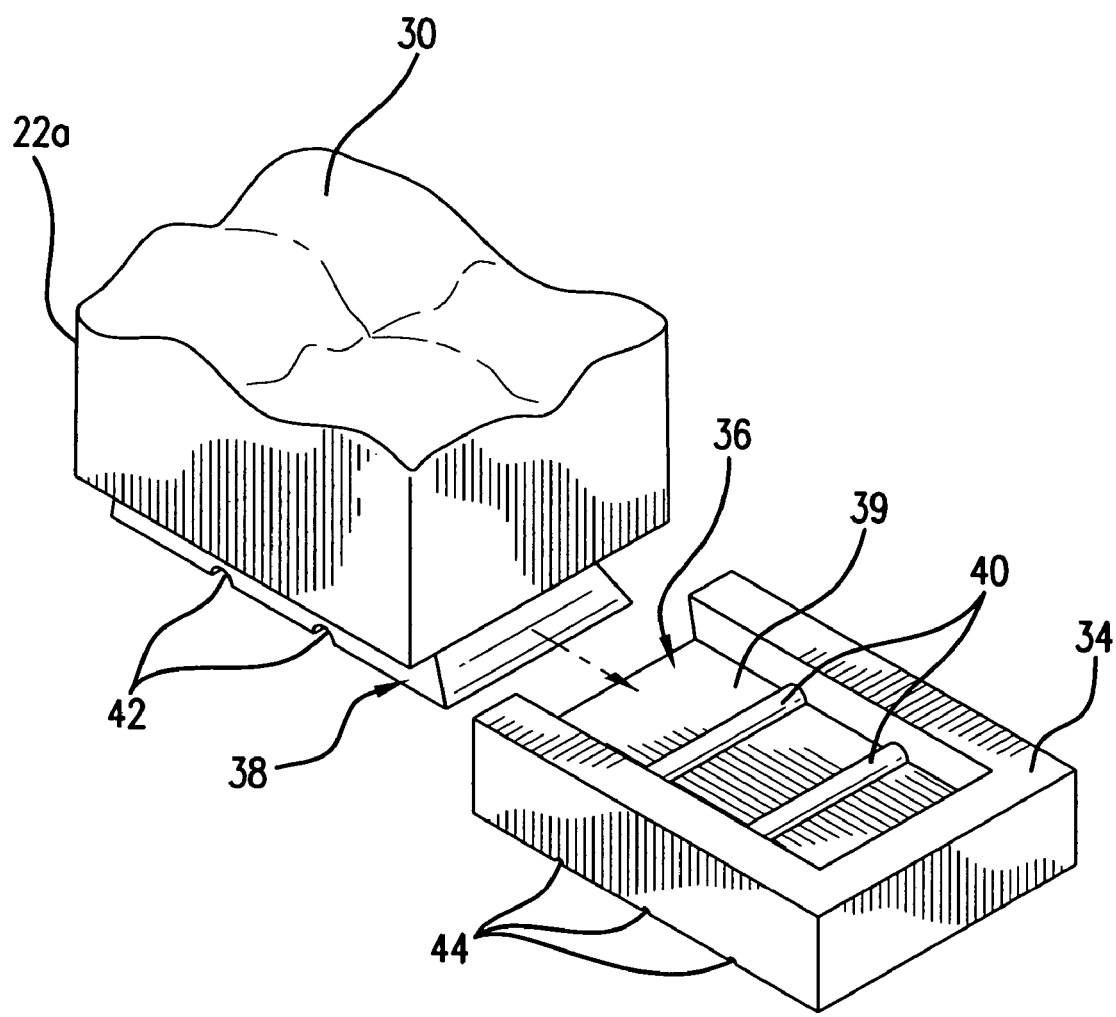
FIG. 2 shows an exploded view of a bite pad and a base member according to the present invention.

A pair of upper bite pads 20a and 20b are carried by upper tray 12 generally located along posterior portion 18 of upper tray 12 on opposite sides from each other. Additionally, a pair of lower bite pads 22a and 22b are carried by lower tray 14 generally along posterior portion 18 of lower tray 14 on opposite sides from each other. Upper bite pads 20a and 20b have a downward projecting bite surface 24, extended from a maxillary occlusal surface 26, best shown in FIG. 4, of upper tray 12. Maxillary occlusal surface 26 faces a mandibular occlusal surface 28 of lower tray 14, which is shown clearly in both FIG. 1 and FIG. 4. Equally, lower bite pads 22a and 22b have an upward projecting bite surface, designated generally as 30, best shown in FIG. 2, extended from mandibular occlusal surface 28 of lower tray 14. Upward projecting bite surface 30, illustrated in FIG. 2, is essentially the same as downward projecting bite surface 24. The difference being that in the preferred embodiment, downward projecting bite surface 24 of upper bite pads 20a and 20b are adapted to conform to the mandibular dentitions in the opposing mandibular occlusal surface 28 of lower tray 14 for cooperative engagement, while upward projecting bite surface 30 of lower bite pads 22a and 22b are adapted to conform to the maxillary dentitions in maxillary occlusal surface 26 of upper tray 12 for cooperative engagement. As is shown in FIG. 2, upward projecting bite surfaces 30, which for illustrative purposes can also represent downward projecting bite surfaces 24, is contoured to the ridges and groves of the opposing engaging teeth on which the pads will bite down. This helps provide a better fit of the appliance to the user which makes the appliance more comfortable for the user to wear.

Figure 3:
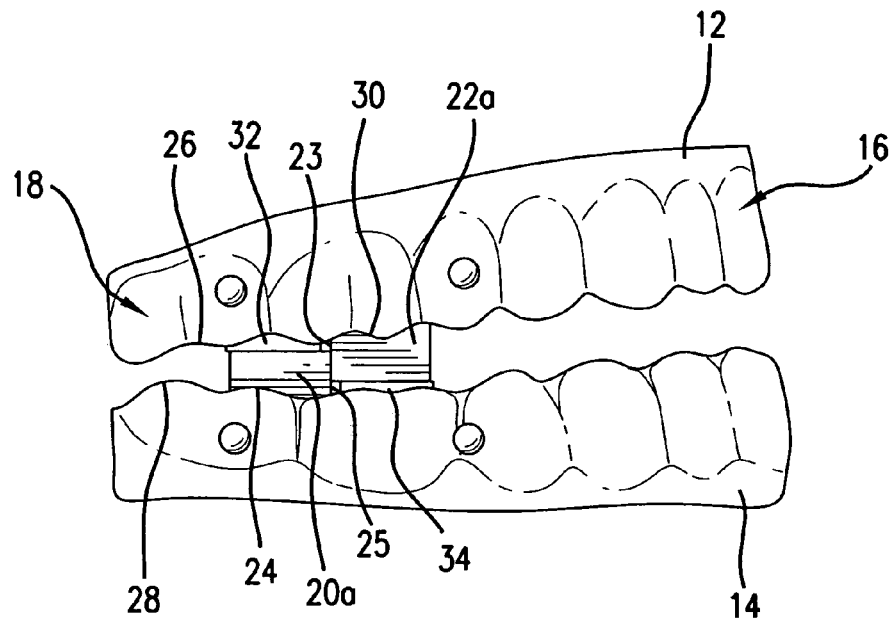
FIG. 3 shows a side elevation view of the dental appliance according to the present invention.

Referring to FIGS. 1 and 3, advantageously, lower bite pads 22a and 22b are located anterior to upper bite pads 20a and 20b within the user's mouth so that upward projecting bite surfaces 30 of lower bite pads 22a and 22b are free to engage maxillary occlusal surface 26 of upper tray 12. Equally, downward projecting bite surfaces 24 of upper bite pad 20a and 20b are free to engage mandibular occlusal surface 28 of lower tray 14 to maintain the occlusal surfaces 26 and 28 of the trays in a predetermined vertically spaced relationship to open the jaws. The bite surfaces of the upper and lower bite pads are not intended to engage each other as the jaw would be forced open beyond a desired amount. Accordingly, as noted above, the pads are staggered to prevent direct engagement of the biting surfaces. Advantageously, as illustrated in FIGS. 1 and 3, the upper and lower bite pads are arranged to abut each other so that distal surface 23 of lower bite pad 22a abuts against mesial surface 25 of upper bite pad 20a. This disto-mesial engagement of the pads is used to advance the mandible by staggering the pads in such a manner as to force the lower jaw forward when the pads abut. The amount of forward movement of the lower jaw, as well as vertical spacing of upper tray 12 and lower tray 14 is determined by the shape and size of the pads, which can be adapted to best serve the particular user. Further, this disto-mesial engagement prevents posterior movement of the mandible while allowing the mandible lateral and vertical flexibility since the trays are not locked together. Allowing for some lateral and vertical flexibility relieves the user's jaw muscles of stress, and generally provides for a much more comfortable and user friendly dental appliance. Preferably, the upper and lower bite pads are made of methyl methacrylate, which is easily sculpted to make particular shape modifications and other fitting adjustments to adapt the pads to the user's specific corrective needs. As with the trays, the pads are not limited to being made of a specific plastic, but rather may be made of any material suitable to carrying out the present invention.

While the upper and lower bite pads may be molded as part of their respective upper and lower trays, in a further advantageous embodiment, upper bite pads 20a and 20b, as well as lower bite pads 22a and 22b are releasably carried by the trays for interchanging different sizes and shapes of bite pads to customize corrective adjustments resulting from the appliance to the specific needs of the user's mouth.

To provide the releasable function for the bite pads, the dental appliance includes an upper base member 32 carried on maxillary occlusal surface 26 of upper tray 12, and a lower base member 34 carried on mandibular occlusal surface 28 of lower tray 14. Upper base member 32 and lower base member 34 are adapted for releasably interconnecting with the upper and lower bite pads, respectively. Referring to FIGS. 5–10, the bite pads and base members are illustrated in detail. Generally, upper and lower base members 32 and 34 include a first locking part, designated generally as 36. The bite pads include a second locking part, designated generally as 38, adapted for cooperating with first locking part 36 of the base members to releasably interconnect the pads to the base members on both the upper and lower trays. Each of the bite pads and base members is of the same construction and arrangement as provide in the Figures and described herein. However, as noted above, the shape of the pads can be modified as desired to conform to the shape of the teeth the bite pad will engage, as well as to adjust the vertical spacing between the trays and advancement of the mandible.

In a preferred embodiment, first locking part 36 of the base members comprises a dovetailed keyway. Second locking part 38 of the pads comprises a dovetailed key for engaging the dovetailed keyway. As best shown in FIG. 2, dovetailed key 38 of bite pad 22a is slid into dovetailed keyway 36 of base member 34. To secure the bite pads to the base members, a pair of ridges 40 are provided along face 39 in the dovetailed keyway which run transverse to the direction in which bite pad 22a is inserted into the dovetailed keyway. To compliment ridges 40, bite pad 22a includes a pair of grooves 42 in dovetailed key 38, which receive the pair of ridges 40. Accordingly, by way of example as shown in FIG. 2, bite pad 22a is slid into dovetailed keyway 36 with sufficient play between the dovetailed keyway and complimentary dovetailed key 38 of pad 22a that key 38 slides over ridges 40 to allow grooves 42 to receive ridges 40 and further lock bite pad 22a to base member 34. This arrangement is applied to all bite pad and base members of the upper and lower trays.

Upper base members 32 and lower base member 34 are typically cemented to their respective occlusal surface of each of trays 12 and 14 using materials and techniques commonly known to those skilled in the art. To help attach the base members to the trays, the bottom side of the base member which is cemented to the occlusal surface of the tray includes a plurality of cementing grooves 44, best shown in FIG. 9, which provides for a tighter bond between the cement, base member, and tray as opposed to a flat surface on the bottom of the base members. Alteratively, it is also possible to simply mold the base members as part of the upper and lower trays, which entirely eliminates the need for cementing the base members to the trays. However, molding the base members to the trays does not provide for as much adaptability to adjust the position of the bite pads and base members to accommodate the corrective needs of the user.

Figure 4:
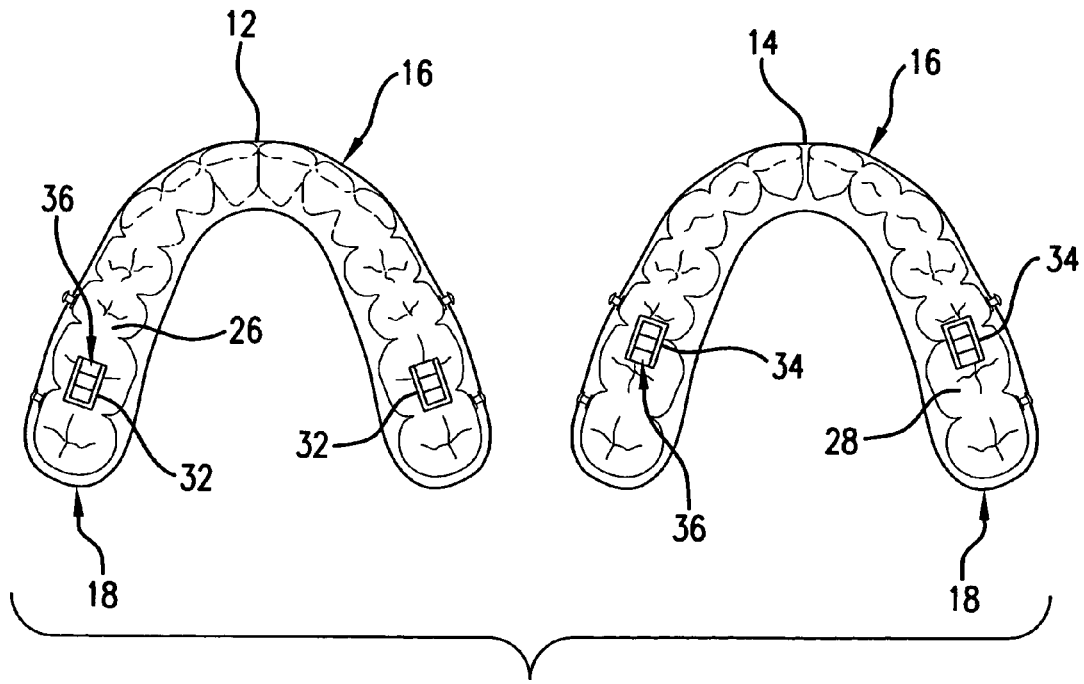
FIG. 4 shows a view of the occlusal surface of the upper and lower trays according to the present invention.

Referring to FIG. 4, it is shown that upper base members 32 carried on upper tray 12 have the opening of dovetailed keyway 36 facing in an anterior direction towards the front teeth. Conversely, lower base members 34 carried on lower tray 14 are turned in the opposite direction to have the opening of dovetailed keyway 36 facing in a posterior direction towards the rear teeth. Advantageously, when the upper and lower bite pads are inserted into their respective base members, the force of the bite pads abutting against each other, in the disto-mesial orientation described above, pushes upper bite pads 20a and 20b towards the posterior 18 of the mouth and lower bite pads 22a and 22b towards the anterior 16 of the mouth, which also pushed dovetailed keys 38 into the dovetailed keyways 36 of the base members, instead of in an outward direction that might dislodge the keys from the keyways. Aligning the base members in this arrangement helps to maintain the bite pads attached to the base members so that there is no accidental release of a bite pad.

Figure 11:
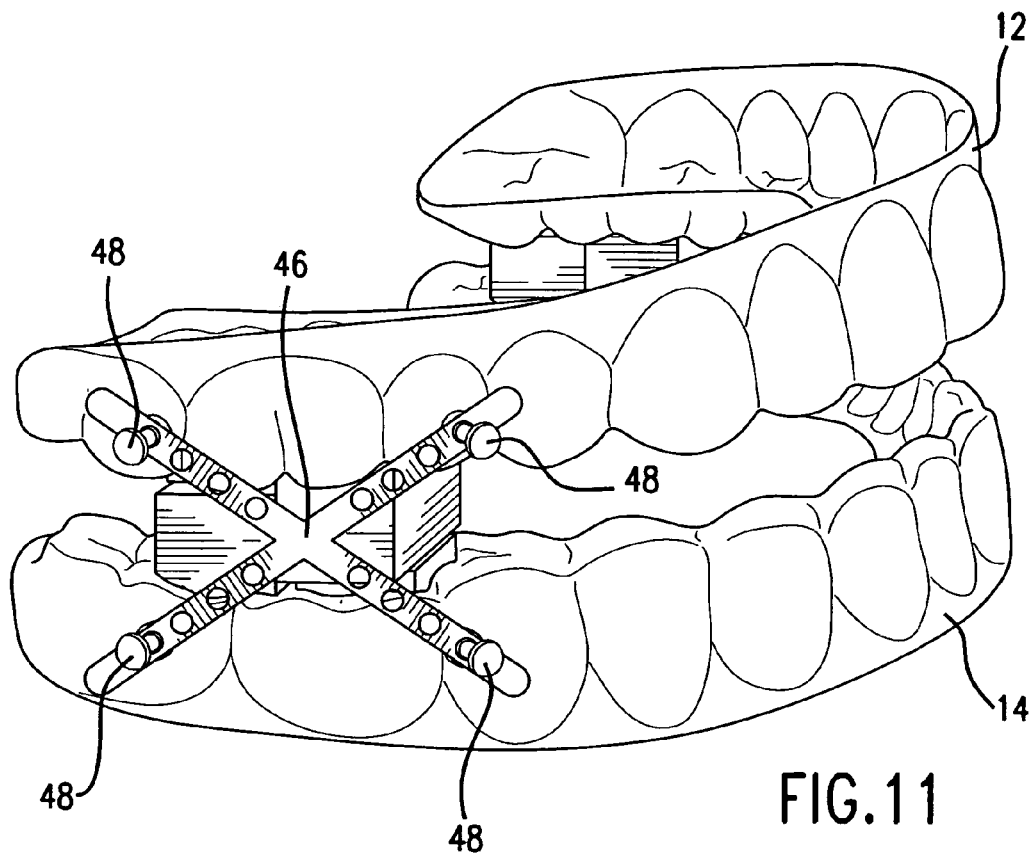
FIG. 11 shows a perspective view of the dental appliance including an elastic band according to the present invention.
Figure 12:
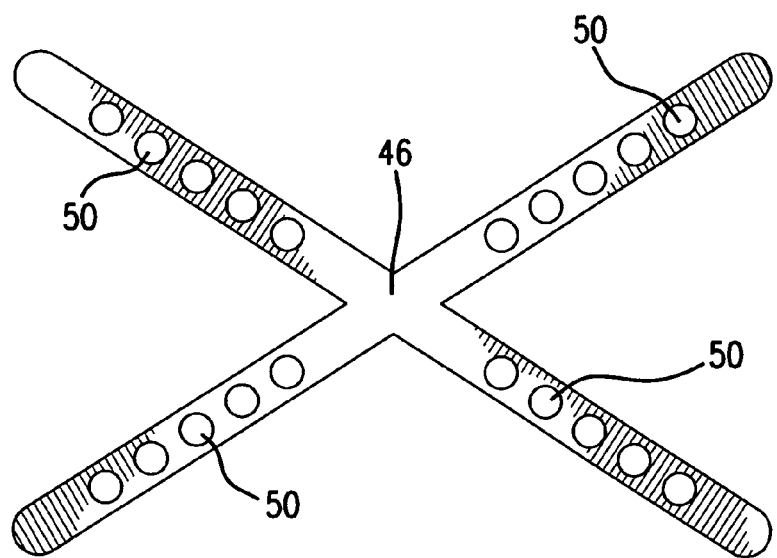
FIG. 12 shows a side view of the elastic band according to the present invention.

Referring to FIGS. 11–14, advantageously, each side of the dental appliance includes an elastic band 46 that interconnects upper tray 12 with lower tray 14 around the area of the bite pads to limit separation of the trays and prevent the lower bite pads from avoiding the upper bite pads and moving posteriorly as a result of excessive vertical movement. To attach the elastic band to the trays, buttons 48 are carried by the upper tray and the lower tray for engaging the elastic band. As best shown in FIG. 11, elastic band 46 engages and extends between the upper and lower buttons to interconnect the trays. The elasticity of band 46 provides the limited vertical movement which relieves tension in the jaw muscles and makes the appliance more comfortable to wear. Preferably, the elastic band is x-shaped for interconnecting with a pair of upper buttons carried by upper tray 12 and a pair of lower buttons carried by lower tray 14. Advantageously, the x-shaped elastic band 46 includes a series of button receiving openings 50 along each leg of the elastic band. As the lower jaw is moved forward or back depending on the size and arrangement of the bite pads, it is necessary to adjust the length at which each leg of elastic band 46 extends to engage buttons 48. The series of button receiving openings 50 easily allows for the tension of each leg of the x-shaped elastic band to be adjusted to accommodate adjustments to the position of the jaws.

Figure 13:
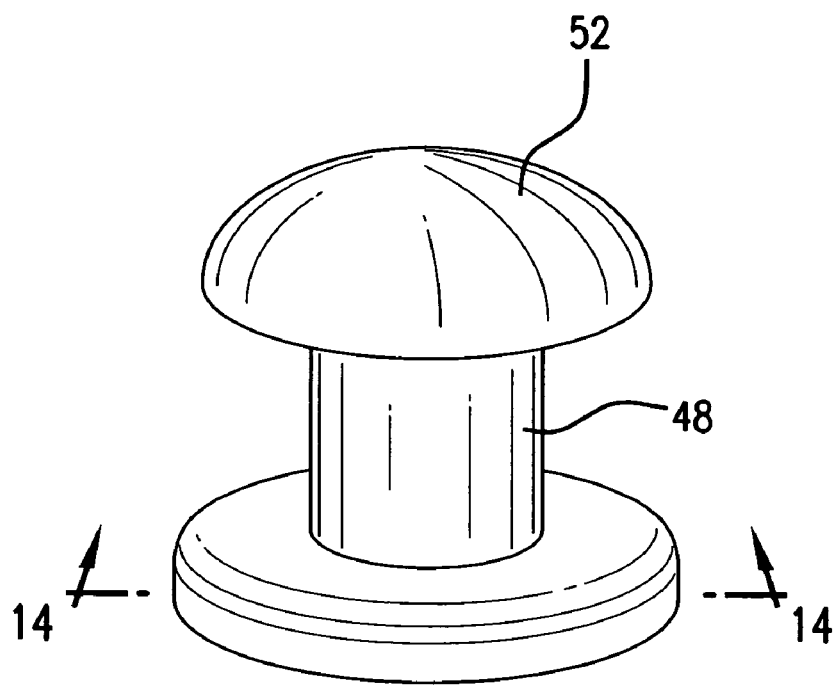
FIG. 13 shows a perspective view of a button carried by the trays according to the present invention; and, FIG. 14 shows a side elevation cross section view of the button according to the present invention.
Figure 14:
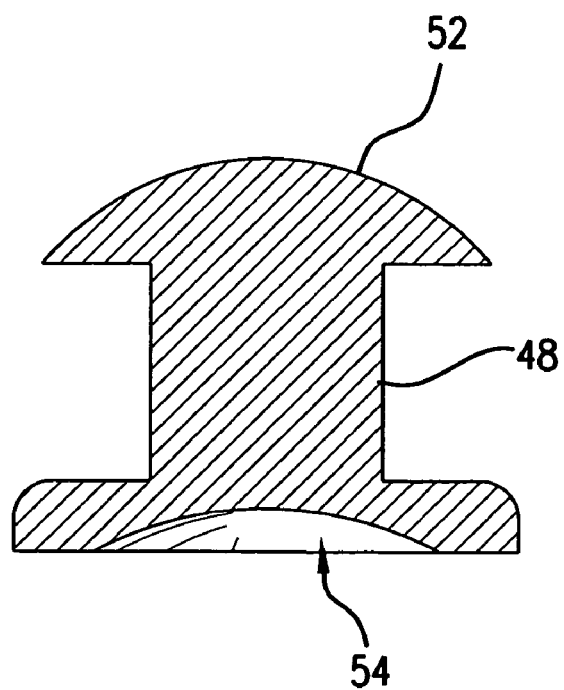

As best shown in FIG. 13, button 48 includes a rounded head 52 which contacts the interior cheek wall. The rounded head helps to prevent any cutting, scraping and catching of the cheek on the dental appliance. Preferably, as shown in FIG. 14, the button includes a concave bottom side 54, which provides space for conforming the bottom of the button to the curved outer surface of the upper and lower trays, as well as providing better adhesion to dental cement for tacking the buttons to the trays by allowing the cement to fill-in underneath the button. Alternatively, however, the button could be molded as part of the upper and lower trays, which as noted above, can have the disadvantage of limiting the adjustable, highly customizable nature of the appliance.

While a preferred embodiment of the invention has been described using specific terms, such description is for illustrative purposes only, and it is to be understood that changes and variations may be made without departing from the spirit or scope of the following claims.

What is claimed is:

1. A dental appliance for spacing the occlusal surfaces of a user's maxillary and mandibular teeth and advancing the mandible, said dental appliance comprising:

an upper tray for receiving the maxillary teeth;

a lower tray for receiving the mandibular teeth;

at least one upper bite pad carried by said upper tray having a downward projecting bite surface extended from a maxillary occlusal surface of said upper tray;

at least one lower bite pad carried by said lower tray having an upward projecting bite surface extended from a mandibular occlusal surface of said lower tray;

said lower bite pad located anterior to said upper bite pad within the user's mouth so that said upward projecting bite surface of said lower bite pad is free to engage said maxillary occlusal surface of said upper tray, and said downward projecting bite surface of said upper bite pad is free to engage said mandibular occlusal surface of said lower tray to maintain said occlusal surfaces of the trays in a predetermined spaced relationship; and, said upper and lower bite pads arranged to abut each other for advancing the mandible and preventing posterior movement of the mandible while allowing the mandible lateral and vertical flexibility.

2. The dental appliance of claim 1 wherein said upper and lower bite pads are releasably carried by said trays for interchanging different sizes and shapes of bite pads to customize corrective adjustments resulting from the appliance to the specific needs of the user's mouth.

3. The dental appliance of claim 2 including an upper base member carried on the maxillary occlusal surface of said upper tray, and a lower base member carried on the mandibular occlusal surface of said lower tray; said upper base member and said lower base member adapted for releasably interconnecting with said upper and lower bite pads, respectively.

4. The dental appliance of claim 3 wherein said upper and lower base members include a first locking part, and said bite pads include a second locking part adapted for cooperating with said first locking part of said base members to releasably interconnect said pads to said base members.

5. The dental appliance of claim 4 wherein said first locking part of said base members comprises a dovetailed keyway, and said second locking part of said pads comprises a dovetailed key for engaging said dovetailed keyway.

6. The dental appliance of claim 1 including at least one elastic band interconnecting said upper tray with said lower tray to limit separation of said trays and prevent said lower bite pad from avoiding said upper bite pad and moving posteriorly.

7. The dental appliance of claim 6 including at least one upper button carried by said upper tray and at least one lower button carried by said lower tray; said elastic band engaging and extending between said upper and lower buttons to interconnect said trays.

8. The dental appliance of claim 7 wherein said elastic band is x-shaped for interconnecting with a plurality of upper and lower buttons carried by said trays.

9. The dental appliance of claim 1 wherein said upper and lower trays are adapted to conform to the user's maxillary and mandibular dentitions, respectively, for holding the trays in place against the user's teeth.

10. The dental appliance of claim 9 wherein said downward projecting bite surface of said upper bite pad is adapted to conform to the mandibular dentitions in the opposing mandibular occlusal surface of said lower tray for cooperative engagement, and upward projecting bite surface of said lower bite pad is adapted to conform to the maxillary dentitions in the maxillary occlusal surface of said upper tray for cooperative engagement.

11. A dental appliance comprising:
an upper tray for fitting to a user's maxillary teeth;
a lower tray for fitting to the user's mandibular teeth;
an upper bite pad carried by a maxillary occlusal surface of said upper tray;
a lower bite pad carried by a mandibular occlusal surface of said lower tray;
said upper and lower bite pads staggered to position said lower bite pad anterior to said upper bite pad so that said lower bite pad is free to engage said maxillary occlusal surface of said upper tray, and said upper bite pad is free to engage said mandibular occlusal surface of said lower tray to vertically separate the trays; and,
said upper and lower bite pads arranged to abut each other to prevent posterior movement of the user's mandible when placed in the user's mouth.

12. The dental appliance of claim 11 wherein said upper and lower trays include a first locking part, and said bite pads include a second locking part adapted for cooperating with said first locking part of said trays to releasably interconnect said pads to said trays.

13. The dental appliance of claim 11 including at least one elastic band interconnecting said upper tray with said lower tray to limit separation of said trays and prevent said lower bite pad from avoiding said upper bite pad and moving posteriorly.

14. The dental appliance of claim 11 wherein said upper bite pad is adapted to conform to the mandibular dentitions in the opposing mandibular occlusal surface of said lower tray for cooperative engagement, and said lower bite pad is adapted to conform to the maxillary dentitions in the maxillary occlusal surface of said upper tray for cooperative engagement.

15. A dental appliance comprising:
an upper tray for fitting to a user's maxillary teeth;
a lower tray for fitting to the user's mandibular teeth;
an upper base member carried by a maxillary occlusal surface of said upper tray;
a lower base member carried by a mandibular occlusal surface of said lower tray;
an upper bite pad releasably carried by said upper base member;
a lower bite pad releasably carried by said lower base member;
said upper and lower bite pads staggered to position said lower bite pad anterior to said upper bite pad so that said lower bite pad is free to engage said maxillary occlusal surface of said upper tray, and said upper bite pad is free to engage said mandibular occlusal surface of said lower tray to vertically separate the trays; and,
said upper and lower bite pads arranged to abut each other to prevent posterior movement of the user's mandible when placed in the user's mouth.

16. The dental appliance of claim 15 wherein said upper and lower base members include a first locking part, and said bite pads include a second locking part adapted for cooperating with said first locking part of said base members to releasably interconnect said pads to said base members.

17. The dental appliance of claim 16 wherein said first locking part of said base members comprises a dovetailed keyway, and said second locking part of said pads comprises a dovetailed key for engaging said dovetailed keyway.

18. The dental appliance of claim 15 including at least one elastic band interconnecting said upper tray with said lower tray to limit separation of said trays and prevent said lower bite pad from avoiding said upper bite pad and moving posteriorly.

19. The dental appliance of claim 15 wherein said upper bite pad is adapted to conform to the mandibular dentitions in the opposing mandibular occlusal surface of said lower tray for cooperative engagement, and said lower bite pad is adapted to conform to the maxillary dentitions in the maxillary occlusal surface of said upper tray for cooperative engagement.

* * * * *